United States Patent [19]
Alexander et al.

[11] Patent Number: 5,913,883
[45] Date of Patent: Jun. 22, 1999

[54] THERAPEUTIC FACIAL MASK

[76] Inventors: Dane Alexander; Arrianna Brighton, both of 10755 East Cholla La., Scottsdale, Ariz. 85259

[21] Appl. No.: 08/692,774
[22] Filed: Aug. 6, 1996
[51] Int. Cl.⁶ ...................................................... A01N 5/00
[52] U.S. Cl. .................................. 607/88; 607/91; 606/9; 606/10; 606/13
[58] Field of Search .................................. 607/50, 80, 88, 607/90, 91, 99, 108, 109; 60/27, 28, 2, 3, 9–13

[56] References Cited

U.S. PATENT DOCUMENTS

| | | |
|---|---|---|
| 1,626,617 | 5/1927 | Last . |
| 1,692,669 | 11/1928 | Last . |
| 3,279,468 | 10/1966 | Levine . |
| 3,376,870 | 4/1968 | Yamamoto et al. . |
| 3,971,387 | 7/1976 | Mantell . |
| 5,085,227 | 2/1992 | Ramon . |
| 5,616,140 | 4/1997 | Prescott ...................................... 607/91 |

*Primary Examiner*—Danton D. DeMille
*Assistant Examiner*—David M. Ruddy
*Attorney, Agent, or Firm*—Parsons & Goltry; Robert A. Parsons; Michael W. Goltry

[57] ABSTRACT

A therapeutic device for supplying beneficial light to organic tissue including a carrier for placement proximate the surface of organic issue, a plurality of light emitting diodes carried by the carrier for substantially uniformly flooding the entire surface of the organic tissue surrounded by the carrier with beneficial light, and a power source, coupled to the carrier, for providing power to the carrier for actuating the light emitting diodes.

9 Claims, 2 Drawing Sheets

THERAPEUTIC FACIAL MASK

BACKGROUND OF THE INVENTION

1. Field of the Invention

This invention relates to therapeutic devices.

More particularly, this invention relates to therapeutic devices for applying therapeutic treatment to organic tissue.

In a further and more specific aspect, the instant invention relates to a therapeutic device for administering beneficial light to organic tissue.

2. Prior Art

The prior art is replete with devices for administering treatment to organic tissues for therapeutic, repair, or beauty treatment purposes. Of particular significance are the various array of therapeutic devices which are suited for treating the skin with the use of electrical energy. Proven to provide significant and beneficial biological and/or therapeutic results, the use of electrical energy to enhance to characteristics of the skin is widely accepted. However, the various therapeutic apparatus available for applying electrical energy to the skin suffer from significant structural and functional shortcomings thereby necessitating certain new and useful improvements.

For instance, all of the known devices operative for providing electrical energy to the skin for facilitating beneficial therapeutic results incorporate electrically conductive elements that engage the surface of the skin, either directly or indirectly. The electrically conductive elements are normally coupled to a power source for energizing the electrically conductive elements. Engagement of the electrically conductive elements to the skin completes the circuit, thereby supplying the skin and surrounding tissue with electrical energy for imparting beneficial therapeutic results.

The inherent shortcoming with the aforementioned therapeutic devices is that in order to facilitate the desired therapy, the surface of the skin must be either in direct or indirect contact with the electrically conductive elements. This can be quite uncomfortable, and can result in irritation of the skin after prolonged contact. Furthermore, the therapeutic benefits of the aforementioned therapeutic devices takes place substantially within only the area where the electrically conductive elements contact the skin. As a result, the beneficial therapeutic results become localized, and unevenly distributed which can be not only ineffective, but also frustrating to the user.

It would be highly advantageous, therefore, to remedy the foregoing and other deficiencies inherent in the prior art.

Accordingly, it is an object of the present invention to provide a therapeutic device for imparting beneficial therapeutic results to organic tissue with the use of beneficial light.

Another object of the present invention is to provide a therapeutic device that is easy to use.

And another object of the present invention is to provide a therapeutic device that is easy to construct.

Still another object of the present invention is to provide therapeutic facial mask for placement proximate the face of an individual for flooding the face with beneficial light.

Yet another object of the instant invention is to provide a therapeutic device that does not need to engage the skin.

Yet still another object of the instant invention is to provide a therapeutic device that is comfortable to use.

And a further object of the invention is to provide a therapeutic device for administering evenly and uniformly distributed therapeutic benefits over a selected area of the skin.

Still a further object of the immediate invention is to provide a therapeutic device that is safe.

Yet a further object of the invention is to provide a therapeutic device for substantially removing wrinkles from skin without contacting the skin.

SUMMARY OF THE INVENTION

Briefly, to achieve the desired objects of the instant invention in accordance with a preferred embodiment thereof, provided is a therapeutic device for supplying beneficial light to organic tissue for imparting beneficial therapeutic affects to the organic tissue, particularly the facial skin of an individual. The therapeutic device includes a mask for substantially encompassing and generally shaped in a manner similar to the average exterior configuration of a range of human facial sizes and shapes. Constructed of acrylic or other similar material, the mask includes a plurality of light emitting diodes. The light emitting diodes are spaced from the surface of the skin and are operative for totally, substantially, and uniformly flooding the entire face of the individual with beneficial light. Also included is a power source, coupled to the mask, for providing power to the mask for actuating the light emitting diodes for facilitating the emission of the beneficial light from the light emitting diodes. The beneficial light can be provided at a specific pulse rate, and is preferably provided at an optimum wavelength of 660 nanometers, although other wavelengths may be used.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which.

DETAILED DESCRIPTION OF THE PREFERRED EMBODIMENT

Figure 1:
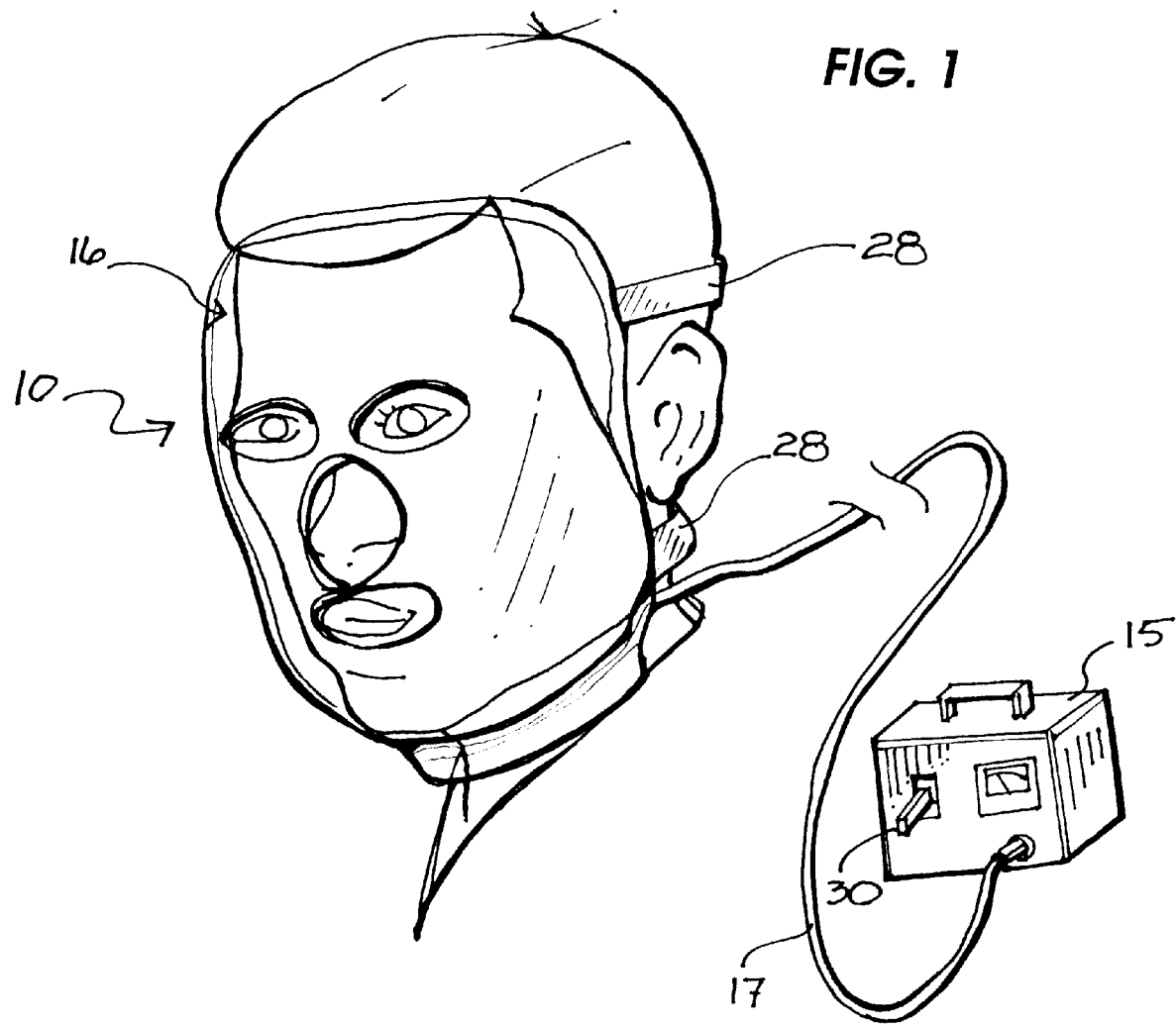
FIG. 1 is a perspective view of a therapeutic facial mask shown as it would appear in use by a human being, the therapeutic mask being shown as it would appear coupled to a power source.

Turning now to the drawings, in which like reference characters indicate corresponding elements throughout the several views, attention is first directed to FIG. 1 which illustrates a preferred embodiment of the instant invention comprising a therapeutic device being generally designated by the reference character 10. Therapeutic device 10 is operative for administering beneficial light to organic tissue for providing beneficial therapeutic results such as the removal of unwanted wrinkles from the skin. Therapeutic device is ideally and preferably suited for administering beneficial therapeutic and healing affects to an individual's facial skin.

As can be seen in FIG. 1, therapeutic device 10 includes an electrical power unit 15 and a carrier or mask 16 for placement proximate the face of an individual. Mask 16 is sized for substantially encompassing the forehead, cheeks, jaw and forward part of the neck of the user. Mask 16 is generally shaped in a manner similar to the average exterior configuration of a range of human facial sizes and shapes. As a result, mask 16 may be used by virtually anybody wishing to use it. Mask 16, constructed of acrylic, plastic, or other substantially similar material, is electrically coupled to electrical power unit 15 by means of electrical power cord 17. Electrical power unit 15 is operative as a power source for supplying electrical power to mask 16 for operation thereof, details of which will be discussed shortly.

Figure 2:
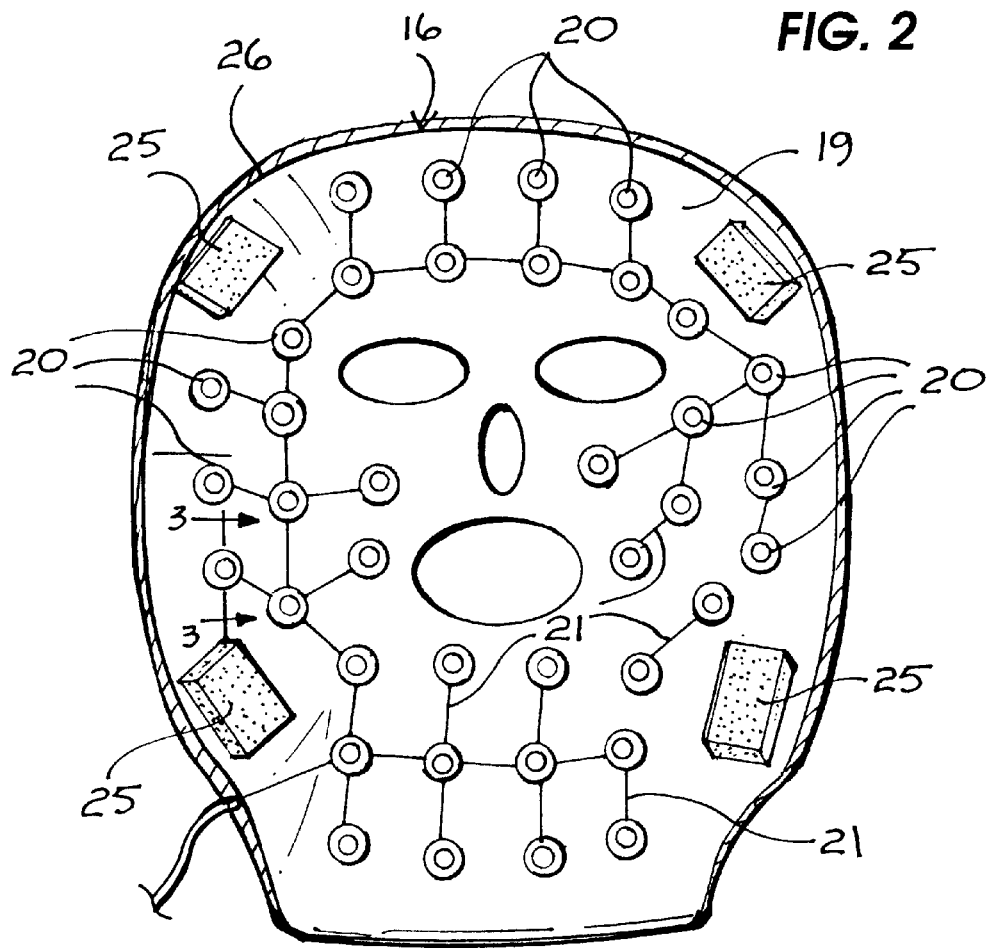
FIG. 2 is a rear view of the therapeutic facial mask shown in FIG. 1.

Attention is now directed to FIG. 2 which illustrates a rear view of mask 16. As can be seen in FIG. 2, mask 16 includes an inner surface 19 and a plurality of conventional light emitting diodes (LED's) 20 carried by mask 16 proximate inner surface 19. The LED's 20 are electrically coupled together by means of conventional electrical interconnections 21, and receive electrical power, conducted through electrical power cord 17, from electrical power unit 15 for actuation thereof. When actuated, LED's 20 emit beneficial light that when directed against the surface of the skin, impart beneficial therapeutic results and healing results.

To use therapeutic device 10, mask 16 is placed proximate the face of an individual, which can clearly be seen in combination with FIG. 1. Pads 25, which may be constructed of foam or other selected material, located near the outer peripheral edge 26 of mask 16 engage portions around the face and hold inner surface 19 of mask 16 and the LED's 20 in spaced apart relation to the surface of the facial skin of the user. Although pads 25 are shown as the preferred means of holding mask 16 in spaced apart relation to the face, any configuration of pads or the like may be used in combination with mask 16 for holding mask 16 in spaced apart relation to the face of the individual without departing from the nature and scope of the instant invention as herein specifically described. Mask 16 is held in place about the head of the individual with a pair of straps 28 coupled thereto which wrap around the head of the user. To administer therapy, electrical power unit 15 is turned on by means of a switch 30 for supplying electrical power to, and thereby actuating, LED's 20 conducted through electrical power cord 17. When actuated, LED's 20 emit beneficial light. The LED's 20 substantially and uniformly flood the entire surface of the skin within the area of mask 16 with the beneficial light which in turn imparts the aforementioned beneficial therapeutic and healing affects.

In order to achieve optimum therapeutic and healing results, the beneficial light is provided at an optimum wavelength of 660 nanometers, although other wavelengths may be used. In addition, the beneficial light can be further provided in the form of pulses generated at a selected rate by electrical power unit 15. Electrical power unit 15 includes conventional electrical components for generating not only power from a power supply element, but also for generating a fluctuating or pulsing output voltage.

The number of LED's 20 provided in combination with mask 16 may be selectively determined depending on the needs of the user. The more LED's 20 used, the more beneficial light will be provided, which is particularly advantageous to those individuals needing intense therapeutic treatment such as the elderly. The less LED's used, the less beneficial light will be provided, which is normally needed for those individuals needing a lower degree of therapeutic treatment such as young people.

Figure 3:
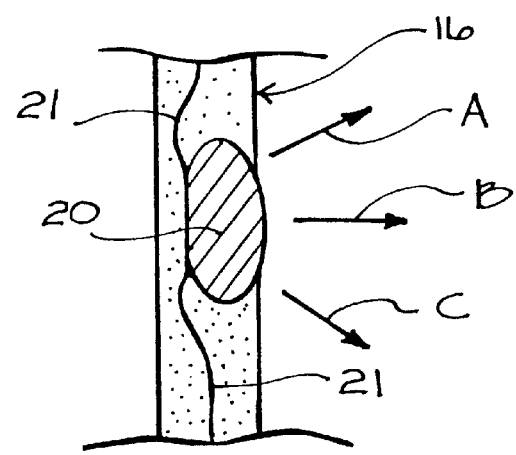
FIG. 3 is a sectional view taken along line 3—3 of FIG. 2.

With attention directed to FIG. 3, each LED 20 and the accompanying electrical interconnections 21 are preferably embedded within mask 16 for ensuring that the LED's 20 do not contact the face. However, LED's 20 and the accompanying electrical interconnections may be carried on inner surface 19 of mask 16 if desired. However, it is important that to achieve the desired beneficial therapeutic affects, LED's 20 be spaced from the surface of the skin so that the beneficial light emanating from each LED 20 indicated by arrows A, B, and C, in FIG. 3, can adequately, substantially, and uniformly flood the skin within the area of mask 16.

Although the instant invention has been specifically described as providing beneficial light to the facial skin of an individual, it will be readily appreciated by those having ordinary skill that therapeutic device 10 may be shaped and/or configured for placement next to any portion of the body needing beneficial therapeutic or healing administration of the beneficial light.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A therapeutic mask for placement proximate the face of an individual for supplying beneficial light to the facial skin, said therapeutic mask comprising:

a mask having a peripheral edge and a shape for substantially encompassing a human face, wherein the shape is substantially maintained during the supplying of the beneficial light;

a plurality of light emitting diodes carried by said mask and spaced apart from the facial skin for substantially uniformly and totally flooding the facial skin of an individual with beneficial light;

spacing elements mounted on the peripheral edge of the mask for maintaining a space between the plurality of light emitting diodes and the facial skin; and a power source, coupled to said mask, for providing power to said mask for actuating said plurality of light emitting diodes.

2. The therapeutic device of claim 1, wherein said plurality of light emitting diodes are mounted proximate an inner surface of said mask.

3. The therapeutic device of claim 1, wherein said plurality of light emitting diodes are embedded within said mask.

4. The therapeutic device of claim 1, wherein said plurality of light emitting diodes are electrically coupled together by means of a plurality of electrical interconnections.

5. The therapeutic device of claim 4, wherein said plurality of electrical interconnections are mounted proximate an inner surface of said carrier.

6. The therapeutic device of claim 4, wherein said plurality of electrical interconnections are embedded within said carrier.

7. The therapeutic device of claim 1, wherein said beneficial light is provided at a 660 nanometer wavelength.

8. The therapeutic device of claim 1, wherein said beneficial light is provided at a selected cyclic rate.

9. The therapeutic device of claim 1, wherein said carrier is constructed of acrylic.

* * * * *